United States Patent
Scott et al.

(10) Patent No.: US 10,399,147 B2
(45) Date of Patent: Sep. 3, 2019

(54) POROUS STRUCTURES AND METHODS OF MAKING SAME

(71) Applicant: Smith & Nephew, Inc., Memphis, TN (US)

(72) Inventors: Marcus L Scott, Ft Worth, TX (US); Lu Gan, Toronto (CA); Vivek D Pawar, Germantown, TN (US); Stanley Tsai, Portland, OR (US)

(73) Assignee: Smith & Nephew, Inc., Memphis, TN (US)

( * ) Notice: Subject to any disclaimer, the term of this patent is extended or adjusted under 35 U.S.C. 154(b) by 602 days.

(21) Appl. No.: 14/379,521

(22) PCT Filed: Feb. 20, 2013

(86) PCT No.: PCT/US2013/026864
§ 371 (c)(1),
(2) Date: Aug. 19, 2014

(87) PCT Pub. No.: WO2013/126407
PCT Pub. Date: Aug. 29, 2013

(65) Prior Publication Data
US 2015/0030493 A1    Jan. 29, 2015

Related U.S. Application Data

(60) Provisional application No. 61/600,963, filed on Feb. 20, 2012.

(51) Int. Cl.
*B22F 3/11*     (2006.01)
*B22F 3/105*    (2006.01)
(Continued)

(52) U.S. Cl.
CPC ............. *B22F 3/1146* (2013.01); *A61L 27/04* (2013.01); *A61L 27/56* (2013.01); *B22F 3/105* (2013.01);
(Continued)

(58) Field of Classification Search
CPC .............................. B22F 3/1146; B33Y 40/00
See application file for complete search history.

(56) References Cited

U.S. PATENT DOCUMENTS 6,215,093 B1   4/2001 Meiners et al.
7,537,664 B2   5/2009 O'Neill et al.
(Continued)

FOREIGN PATENT DOCUMENTS

CN    102205144 A  * 10/2011   ........... A61L 27/047
JP    57-053235 B     3/1982
(Continued)

OTHER PUBLICATIONS

Maekawa, Katsuhiro, Terutake Hayashi, Kenichi Hanyu, Kazunori Umeda, and Takashi Murakami. "The Spark Plasma Sintering Method Using Laminated Titanium Powder Sheet for Fabricating Porous Biocompatible Implants." High Temperature Materials and Processes 26.4 (2007): 285-90. Web. Mar. 15, 2017.*
(Continued)

*Primary Examiner* — Matthew E. Hoban
*Assistant Examiner* — Jeremy C Jones (57) ABSTRACT

The present disclosure provides methods to improve the properties of a porous structure formed by a rapid manufacturing technique. Embodiments of the present disclosure increase the bonding between the micro-particles 5 on the surface of the porous structure and the porous structure itself without substantially reduce the surface area of the micro-particles. In one aspect, embodiments of the present disclo-
(Continued)

sure improves the bonding while preserving or increasing the friction of the structure against adjacent materials.

44 Claims, 5 Drawing Sheets

(51) Int. Cl.
    *B22F 3/24* (2006.01)
    *B29C 65/00* (2006.01)
    *A61L 27/56* (2006.01)
    *A61L 27/04* (2006.01)
    *B33Y 40/00* (2015.01)
    *C22F 1/18* (2006.01)
    *B29C 64/153* (2017.01)
    *B33Y 80/00* (2015.01)
    *B33Y 70/00* (2015.01)
    *B29K 101/00* (2006.01)
    *B29K 105/04* (2006.01)

(52) U.S. Cl.
    CPC .............. *B22F 3/1055* (2013.01); *B22F 3/24* (2013.01); *B29C 64/153* (2017.08); *B29C 66/72* (2013.01); *B33Y 40/00* (2014.12); *C22F 1/18* (2013.01); *B22F 2003/248* (2013.01); *B29K 2101/00* (2013.01); *B29K 2105/04* (2013.01); *B33Y 70/00* (2014.12); *B33Y 80/00* (2014.12); *C04B 2235/6026* (2013.01); *C04B 2235/6584* (2013.01); *C04B 2235/665* (2013.01); *Y02P 10/295* (2015.11)

(56) References Cited

U.S. PATENT DOCUMENTS

| | | | |
|---|---|---|---|
| 8,268,099 B2 | 9/2012 | O'Neill et al. | |
| 8,268,100 B2 | 9/2012 | O'Neill et al. | |
| 8,992,703 B2 | 3/2015 | O'Neill et al. | |
| 9,101,476 B2* | 8/2015 | Deruntz | A61F 2/30734 |
| 9,456,901 B2* | 10/2016 | Jones | A61F 2/2803 |
| 2006/0147332 A1 | 7/2006 | Jones et al. | |
| 2008/0031767 A1* | 2/2008 | Naumann | B01J 23/755 |
| | | | 420/457 |
| 2009/0292365 A1* | 11/2009 | Smith | A61L 27/04 |
| | | | 623/23.55 |
| 2010/0010638 A1* | 1/2010 | Jones | A61F 2/30907 |
| | | | 623/23.12 |
| 2010/0028710 A1* | 2/2010 | Gros | B22F 3/1021 |
| | | | 428/613 |
| 2010/0221136 A1* | 9/2010 | Maffia | B22F 3/1121 |
| | | | 419/2 |
| 2010/0256773 A1* | 10/2010 | Thijs | A61C 8/0006 |
| | | | 623/23.55 |
| 2010/0291401 A1* | 11/2010 | Medina | B23K 15/0086 |
| | | | 428/593 |
| 2013/0011691 A1* | 1/2013 | Ruan | A61L 27/047 |
| | | | 428/566 |
| 2015/0258735 A1 | 9/2015 | O'Neill et al. | |

FOREIGN PATENT DOCUMENTS

| | | |
|---|---|---|
| JP | 2002-038201 A | 2/2002 |
| JP | 2007-262568 A | 10/2007 |

OTHER PUBLICATIONS

Hong, S B et al. "A new Ti—5Ag alloy for customized prostheses by three-dimensional printing (3DP)." Journal of dental research 80 3 (2001): 860-3.*
Stamp, R., et al. "The Development of a Scanning Strategy for the Manufacture of Porous Biomaterials by Selective Laser Melting." SpringerLink, Springer US, Jun. 18, 2009, link.springer.com/article/10.1007%2Fs10856-009-3763-8.*
Li, C. F., et al. "Microhardness of Pore Walls in Porous Titanium Prepared with Novel Powder Metallurgy." Powder Metallurgy, vol. 48, No. 3, Sep. 2005, pp. 237-240. EBSCOhost, doi:10.1179/174329005X64162.*
Japanese Patent Office, dated Feb. 6, 2017, 7 pages, including English Translation.
Australian Patent Office, First Office Action, dated Oct. 30, 2015, 3 pages.
Chinese Patent Office, First Office Action, dated Jul. 2, 2015, 15 pages, including English Translation.
Chinese Patent Office, Second Office Action, dated Apr. 25, 2016, including English translation, 7 pages.
European Patent Office, Search Report, dated Feb. 25, 2016, 9 pages.
China Patent Office, Decision on Rejection dated Jan. 6, 2017, 9 pages, including English Translation.
R. Morgan, A. Papworth, C. Sutcliffe, P. Fox, and W. O'Neill, "Direct Metal Laser Re-Melting of 316L Stainless Steel Powder Part 1: Analysis of Thin Wall Structures," Proceedings of the 2001 Solid Freeform Fabrication Symposium, pp. 276-282, 2001.
R. Morgan, A. Papworth, C. Sutcliffe, P. Fox, and W. O'Neill, "Direct Metal Laser Re-Melting of 316L Stainless Steel Powder Part 2: Analysis of Cubic Primitives," Proceedings of the 2001 Solid Freeform Fabrication Symposium, pp. 283-295, 2001.
R. Morgan, C. Sutcliffe, and W. O'Neill, "Experimental Investigation of Nanosecond Pulsed Nd:YAG Laser Re-Melted Preplaced Powder Beds", Rapid Prototyping Journal, vol. 7, iss. 3, pp. 159-172, 2001.
R. Morgan, A. Papworth, C. Sutcliffe, P. Fox, and W. O'Neill, "High Density Net Shape Components by Direct Laser Re-Melting of Single-Phase Powders," Journal of Materials Science, vol. 37. pp. 3093-3100, 2002.
S.R. Pogson, P. Fox, C.J. Sutcliffe, and W. O'Neil, "The production of copper parts using DMLR," Rapid Prototyping Journal, vol. 9, No. 5, pp. 334-343, 2003.
J.A. Ramos, D.L. Bourell, "Mechanics of the Selective Laser Raster-Scanning Surface Interaction," Proceedings of the 2003 Solid Freeform Fabrication Symposium, pp. 559-572, 2003.
J. Williams, D. Miller, and C. Deckard, "Selective Laser Sintering Part Strength as a Function of Andrew Number, Scan Rate and Spot Size", Proceedings of 1996 Solid Freeform Fabrication Symposium, pp. 549-557, 1996.
J. Williams and C. Deckard, "Advances in Modeling the Effects of Selected Parameters on the SLS Process", Rapid Prototyping Journal, vol. 4 No. 2, pp. 90-100, 1998.
Japanese Decision of Rejection; Japanese Patent Office; Japanese Patent Application No. 2014-557875; dated Jul. 23, 2018; 8 pages.
Chinese Reexamination Decision; Chinese Patent Office; Chinese Patent Application No. 201380009988.1; dated May 28, 2018; 19 pages.
Japanese Notice of Reasons for Rejection; Japanese Patent Office; Japanese Patent Application No. 2014-557875; dated Jan. 5, 2018; 11 pages.
Chinese Notice of Reexamination; Chinese Patent Office; Chinese Patent Application No. 201380009988.1; dated Oct. 27, 2017; 10 pages.

* cited by examiner

POROUS STRUCTURES AND METHODS OF MAKING SAME

CROSS-REFERENCE TO RELATED APPLICATIONS

This application is a United States National Phase filing of International Application No. PCT/US2013/026864, which claims the benefit of U.S. Provisional Application No. 61/600,963, filed Feb. 20, 2012. The disclosure of each prior application is incorporated by reference in its entirety.

FIELD OF INVENTION

The present disclosure generally relates to porous structures produced by rapid manufacturing technologies and/or additive manufacturing technologies and methods of making same, and more particularly to improving the surface properties of the porous structures.

BACKGROUND

Certain medical implants and orthopedic implants require strength for weight bearing purposes and porosity to encourage bone/tissue in-growth. For example, many orthopedic implants include porous sections that provide a scaffold structure to encourage bone in-growth during healing and a weight bearing section intended to render the patient ambulatory more quickly. Rapid manufacturing technologies (RMT), particularly direct metal fabrication (DMF), or direct metal laser sintering (DMLS), and solid free-form fabrication (SFF), have been used to produce metal foam used in medical implants or portions of medical implants. These technologies are also referred to as additive manufacturing technologies. In general, RMT methods allow for structures to be built from 3-D CAD models, including tessellated/triangulated solids and smooth solids. For example, DMF techniques produce three-dimensional structures one layer at a time from a powder which is solidified by irradiating a layer of the powder with an energy source such as a laser or an electron beam. The powder is fused, melted or sintered, by the application of the energy source, which is directed in raster-scan fashion to selected portions of the powder layer. After fusing a pattern in one powder layer, an additional layer of powder is dispensed, and the process is repeated with fusion taking place between the layers, until the desired structure is complete.

Figure 1:
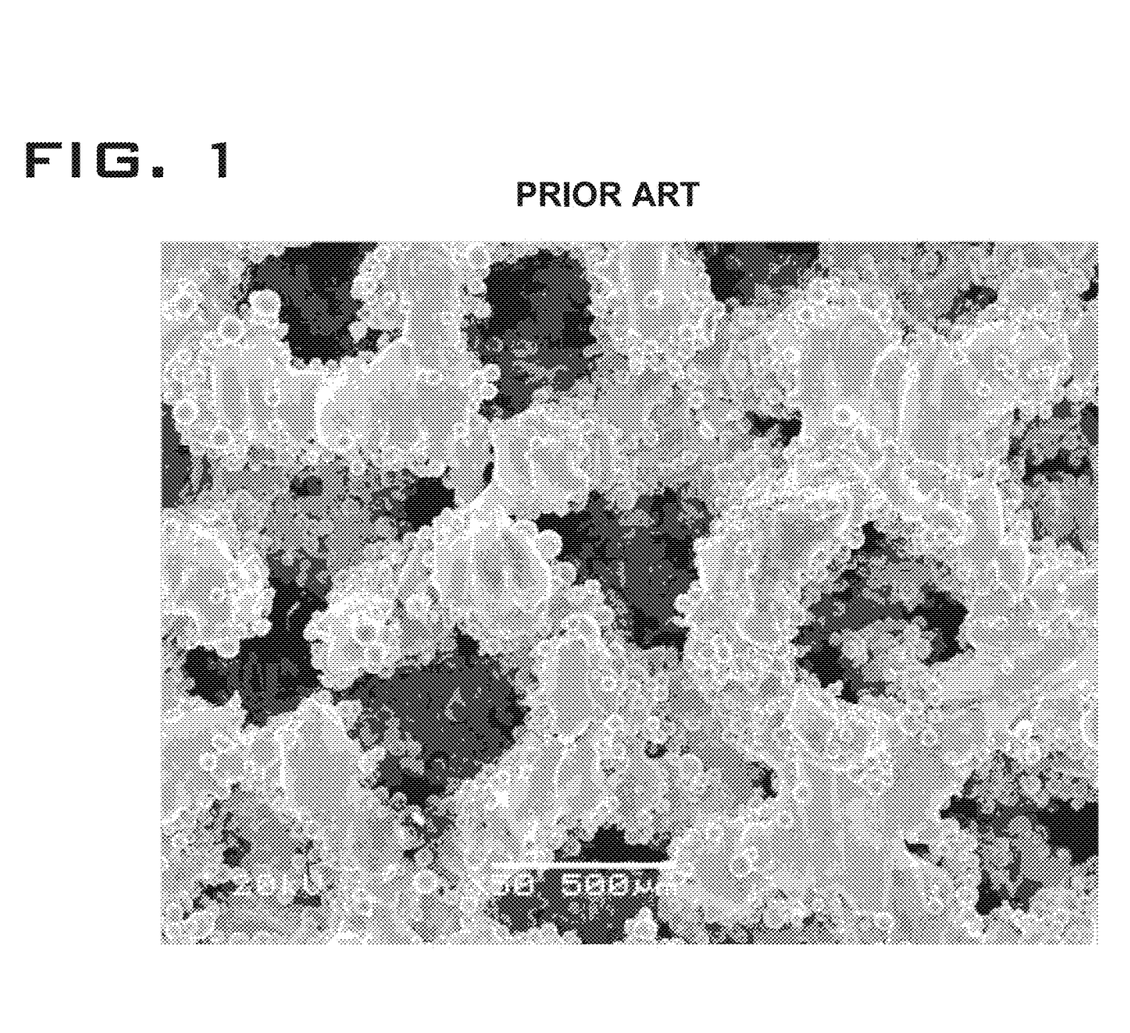
FIG. 1 is a scanning electron microscope (SEM) image of a portion of a porous structure manufactured by rapid manufacturing techniques taken at 50× magnification.

FIG. 1 is a scanning electron microscope (SEM) image of an exemplary porous metal structure built by RMT taken at 50× magnification. As can be seen, such porous metal bone ingrowth structures built by rapid manufacturing techniques comprise fully-molten struts covered with spherical metal micro-particles or beads that are semi-fused or partially fused to the structures. This is because when the laser strikes the powder, it creates a melt pool in which the powder is melted into liquid form and melded to the adjoining area. However, at the very edge of the melt pool, some of the powder particles do not completely melt into liquid form. As a result, after cooling, the surface of the porous structures often contain residual powder particles that are only partially attached to the structure.

When the porous structure is used in a medical implant, these semi-fused micro-particles have the benefit of increasing surface area of the porous structure for cellular attachment and subsequent bone ingrowth in vivo. If these particles are too loosely bound, however, they can detach during implantation or use (e.g., due to micro-motion between the bone and porous structure) and migrate to the joint space, possibly acting as a third body particle and increasing wear of the implant bearing surfaces. Typical post-manufacturing processes, such as machining or polishing, to finish the surface and remove the attached powder particles are not available for porous structures due to the porosity nature of these structures where internal struts or surfaces are out of reach. Furthermore, these post-manufacturing processes pose a contamination concern because machine oil and reagents used in such processes may adversely affect the bone-ingrowth if not adequately removed.

Known post-manufacturing processes to address these micro-particles include removal of the micro-particles by chemical etching, such as that disclosed in U.S. Application Publication No. 2006/0147332, or melting them into the main body of the porous structure, such as that disclosed by Stamp et al (J Master Sci: Mater. Med (2009) 20:1839-48). While these methods ensure that the micro-particles do not detach and harm the patient during use, they also diminish the benefits provided by these micro-particles by reducing the surface area and the asperities of the porous structure for cellular attachment.

In light of the above, there is still a need for efficient methods to improve the attachment strength of the micro-particles without substantially reducing the surface area, asperities, and/or friction of the porous structure for certain benefits, such as cellular attachment and initial fixation.

SUMMARY OF THE DISCLOSURE

In accordance with one aspect of the invention, there is provided a method comprising the step of: treating a porous structure formed by rapid manufacturing technique with a thermal treatment to increase the bond strength between a plurality of micro-particles attached to said porous structure and said porous structure without substantially reducing the surface area of the porous structure.

In one embodiment, the thermal treatment provides average micro-particle diameter to neck diameter ratio greater than 1 and less than 5.

In one embodiment, the thermal treatment is selected from the group consisting of high vacuum furnace treatment, resistive heat treatment, radiative heat treatment, electron beam scanning, laser beam scanning, and a combination thereof.

In one embodiment, the thermal treatment is performed for a selected time and temperature.

In another embodiment, the method further comprises the step of selecting the time and temperature for said thermal treatment, wherein said selection is configured to improve the bonding between said plurality of micro-particles and said porous structure while at least substantially preserving a desired roughness and friction of said porous structure.

In another embodiment, the method further comprises the step of selecting the time and temperature for said thermal treatment, wherein said selection is configured to improve the bonding between said plurality of micro-particles and said porous structure while increasing the roughness of said porous structure.

In one embodiment, the plurality of micro-particles comprises a powder selected from the group consisting of metal, ceramic, metal-ceramic (cermet), glass, glass-ceramic, polymer, composite and combinations thereof. In one embodiment, the metallic material is selected from the group consisting of titanium, titanium alloy, zirconium, zirconium alloy, niobium, niobium alloy, tantalum, tantalum alloy, nickel-chromium (e.g., stainless steel), cobalt-chromium alloy and combinations thereof.

In one embodiment wherein the porous structure comprises titanium alloy, the temperature of the thermal treatment of the titanium alloy structure is between greater than about 800 degrees C. and about 1200 degrees C. In another embodiment, the temperature of the thermal treatment of the titanium alloy structure is between about 950 degrees C. and about 1150 degrees C. In another embodiment, the temperature of the thermal treatment of the titanium alloy structure is between about 1000 degrees C. and about 1100 degrees C. In another embodiment, the temperature of the thermal treatment of the titanium alloy structure is between about 1025 degrees C. and about 1075 degrees C. In another embodiment, the temperature of the thermal treatment of the titanium alloy structure is between about 1040 degrees C. and about 1060 degrees C. In another embodiment, the temperature of the thermal treatment of the titanium alloy structure is about 1050 degrees C.

In one embodiment, the porous structure is thermally treated from about 30 minutes to 300 minutes. In another embodiment, the porous structure is thermally treated from about 60 minutes to 180 minutes. In another embodiment, the porous structure is thermally treated from about 90 minutes to 150 minutes. In yet another embodiment, the porous structure is thermally treated for about 120 minutes.

In one embodiment, the thermal treatment is performed in a vacuum or inert gas furnace below atmospheric pressure, e.g., about 1 atm or about 0.21 oxygen partial pressure. In another embodiment, the thermal treatment is performed in a vacuum or inert gas furnace with oxygen partial pressure below about 0.02 torr. In another embodiment, the thermal treatment is performed in a vacuum or inert gas furnace with oxygen partial pressure below about $10^{-4}$ torr. In yet another embodiment, the thermal treatment is performed in a vacuum or inert gas furnace with oxygen partial pressure at or below about $10^{-5}$ torr.

In one embodiment, the time and temperature of the thermal treatment is determined based at least on the size of the plurality of micro-particles and the solid-state diffusion coefficient of the plurality of micro-particles.

In one embodiment, the time and temperature of the thermal treatment is determined based at least on the desired aspect ratio of the porous structure.

In one embodiment, the time and temperature of the thermal treatment is determined based at least on the desired friction of a surface of the porous structure.

In another embodiment, the method comprises the step of forming a medical implant with said treated porous structure. In one embodiment, the medical implant is selected from the group consisting an orthopedic implant, dental implant, and vascular implant.

In one embodiment, the selecting step comprises determining a friction value of said porous structure prior to treatment, determining a friction value of said porous structure subsequent to treatment, adjusting the time and temperature of said treatment until the friction value prior to treatment is at least substantially the same as the friction value subsequent to treatment.

In one embodiment, the selecting step comprises determining a friction value of said porous structure prior to treatment, determining a friction value of said porous structure subsequent to treatment, adjusting the time and temperature of said treatment until the friction value subsequent to treatment is higher than said friction value prior to treatment.

In one embodiment, the selected time and temperature for said treatment results in the friction value prior to treatment being within about 0% to less than about 15% of the friction value subsequent to treatment. In another embodiment, the selected time and temperature for said treatment results in the friction value prior to treatment being within about 5% to about 10% of the friction value subsequent to treatment. In another embodiment, the selected time and temperature for said treatment results in the friction value prior to treatment being within about 10% to less than about 15% of the friction value subsequent to treatment. In another embodiment, the selected time and temperature for said treatment results in the friction value prior to treatment being within about 8% to about 12% of the friction value subsequent to treatment.

In one embodiment, the friction value comprises a coefficient of friction when said porous structure is articulated against an analogue component.

In one embodiment, the friction and or roughness of structure is measured using an inclined plane method as described by Heiner and Brown, $53^{rd}$ ORS, 2007 or using a pin-on-disk testing apparatus described in Gilmour et al, World Biomaterials Congress (WBM), a conference organized by the Society for Biomaterials (SFB), 2008, the disclosures of both are incorporated by reference. In one embodiment, the pin-on-disk method provides the friction value at the beginning of the motion and also during the motion.

Other advantages and features will be apparent from the following detailed description when read in conjunction with the attached drawings. The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the disclosed methods and apparatuses, reference should be made to the embodiments illustrated in greater detail in the accompanying drawings, wherein.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION

The present disclosure provides for methods to address improve the attachment strength, or bonding, of the micro-particles to a porous structure without substantially reducing the surface area or friction of the porous structure to attain desirable properties, such as an optimal friction or roughness for cellular attachment and initial fixation. The rougher structure due to higher friction is more stable and prevents the micro-motion against the bone and thus is considered beneficial for early stability and bone-ingrowth. Due to the build technique of melting powder particles to fuse them together, a porous structure built by RMT often contains residual powder particles that are either loose or partially fused (semi-fused) to the surface of the porous structure. These loose or semi-fused particles provide certain beneficial properties, such as porosity or surface area that allow for cellular growth; however, they can be harmful if they detach in the patient's body when the porous structure is articulated against an analogue implant component or the patient's bone.

According to one aspect of the present disclosure, to increase the bonding or attachment strength of these powder particles or micro-particles while maintaining the surface area of the micro-particles, the porous structure formed by RMT undergoes a thermal treatment. The porous structure is exposed to a thermal treatment having a certain temperature and pressure for a certain duration that is sufficient to increase the bond strength of the micro-particles to the main body of the porous structure without substantially reducing the surface area of the porous structure. In the preferred embodiment, the thermal treatment comprises a high vacuum furnace treatment. However, other embodiments contemplate employing similar thermal techniques known to those skilled in the art such as resistive heat treatment, including spark plasma sintering or other appropriate methods, radiative heat treatment, including white light radiation, electron beam scanning, or laser beam scanning.

According to one aspect of the present disclosure, the thermal treatment is controlled to ensure that the micro-particles are not completely melted into the main body of the porous structure, which would reduce the surface area of the porous structure. In the preferred embodiment, appropriate conditions of the thermal treatment can be determined by selecting parameters that preserve or increase the surface area, friction and/or asperities of the porous structure when it articulates against an analogue component.

Determining the asperities of the porous structure is another way of characterizing the desired properties for certain benefits, such as cellular attachment and initial fixation. The asperities are peaks of material that stand proud of the core structure. The aspect ratio of asperities can be defined as height of the peak above the core structure (or strut) to the maximum width of the asperity itself. Based on the particle size, the asperities can be rounded (e.g., aspect ratio approaching or less than 1) or could be sharp (e.g., aspect ratio>1).

Because the micro-particles are residual particles that did not melt during the RMT process, the micro-particles comprise the same material as the porous structure itself. In one embodiment, the plurality of micro-particles comprises a powder selected from the group consisting of metal, ceramic, metal-ceramic (cermet), glass, glass-ceramic, polymer, composite and combinations thereof. In one embodiment, the metallic material is selected from the group consisting of titanium, titanium alloy, zirconium, zirconium alloy, niobium, niobium alloy, tantalum, tantalum alloy, nickel-chromium (e.g., stainless steel), cobalt-chromium alloy and combinations thereof.

In one specific embodiment of the present disclosure, the porous structure comprises titanium alloy. To the temperature of the thermal treatment of the titanium alloy structure is between greater than about 800 degrees C. and about 1200 degrees C. In another embodiment, the temperature of the thermal treatment of the titanium alloy structure is between about 950 degrees C. and about 1150 degrees C. In another embodiment, the temperature of the thermal treatment of the titanium alloy structure is between about 1000 degrees C. and about 1100 degrees C. In another embodiment, the temperature of the thermal treatment of the titanium alloy structure is between about 1025 degrees C. and about 1075 degrees C. In another embodiment, the temperature of the thermal treatment of the titanium alloy structure is between about 1040 degrees C. and about 1060 degrees C. In the preferred embodiment, the temperature of the thermal treatment is about 1050 degrees C.

The duration of the heat-treatment can range from preferably about 30 minutes to about 300 minutes, more preferably from about 60 minutes to about 180 minutes and from about 90 minutes to about 150 minutes, and most preferably about 120 minutes. The heat-treatment is carried out in a vacuum or inert gas furnace at preferably below atmospheric pressure, e.g., about 1 atm or about 0.21 oxygen partial pressure. In another embodiment, the thermal treatment is performed in a vacuum or inert gas furnace with oxygen partial pressure preferably below about 0.02 torr and more preferably below about $10^{-4}$ torr, and most preferably at or below about $10^{-5}$ torr.

According to another aspect, the duration (or treatment time) and temperature is based at least on the size and the solid-state diffusion coefficient of the micro-particles. Although not intending to be bound by theory, the inventors believe this is due to the sintering of particle on the strut being a function of the material melting point and size of the particle.

Figure 3:
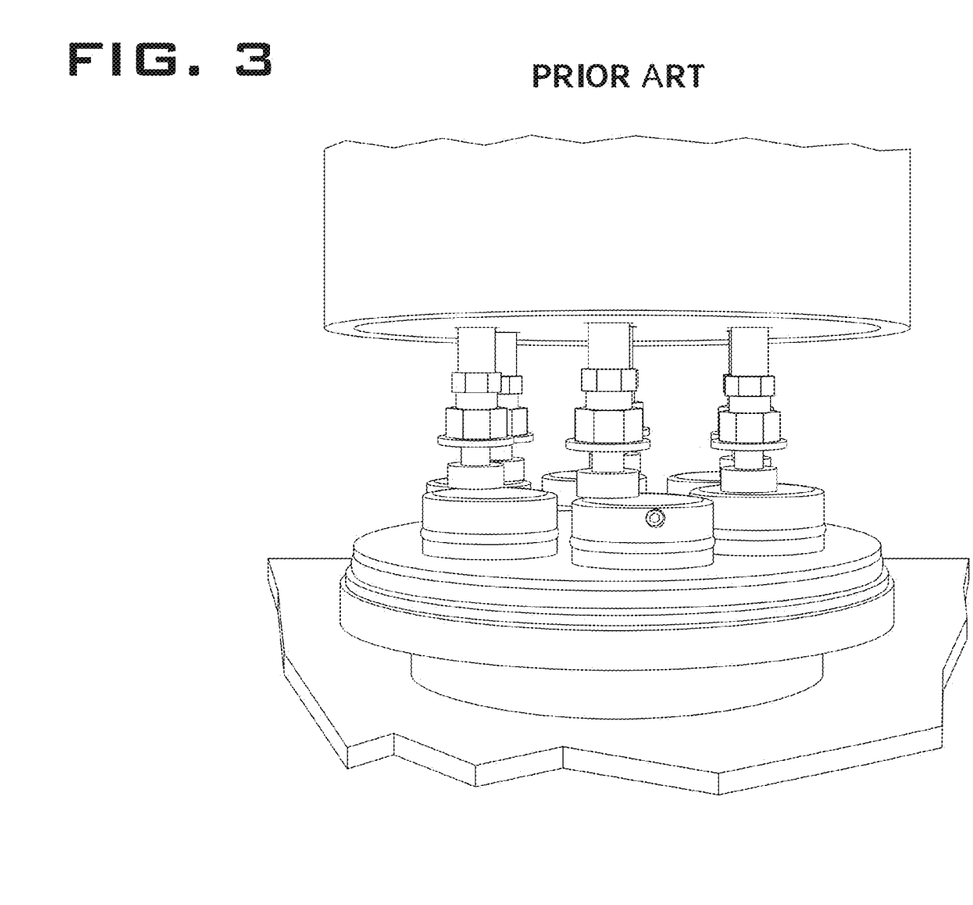
FIG. 3 is a photograph of an exemplary pin and disc testing equipment.

The friction and roughness of structure can be measured by methods known to those skilled in the art. One exemplary method is an inclined plane method as described by Heiner and Brown, 53rd ORS, 2007. Another exemplary method is a pin-on-disk testing apparatus, which is described in Gilmour et al., WBM, 2008. In either of these methods either bone analogue material or a cadaveric specimen can be used. The inclined plane method provides friction information at the beginning of the motion but not necessary during the motion. The pin-on-disk method provides information for both at the beginning of the motion and during the motion. FIG. 3 is a photograph of an exemplary equipment to perform the pin-on-disk method. Typically, in a pin-on-disk method, a vertical normal load of 44 N (0.15 MPa) is applied to the pins made from porous structure. The pins are attached to the upper fixture of the pin-on-disk machine shown in FIG. 3. The machine is programmed such that the base plate rotates all bone analogue plates in an arc shaped motion path at a displacement rate of about 3.8 mm/sec. Vertical and horizontal loads are sampled at 100 Hz and are then used to calculate the maximum dynamic coefficient of friction (tangential force divided by normal force). These test parameters are provided for exemplary purposes and are not intended to be limiting. The parameters and conditions can be varied as appropriate based on the porous structure and testing goals.

Figure 2:
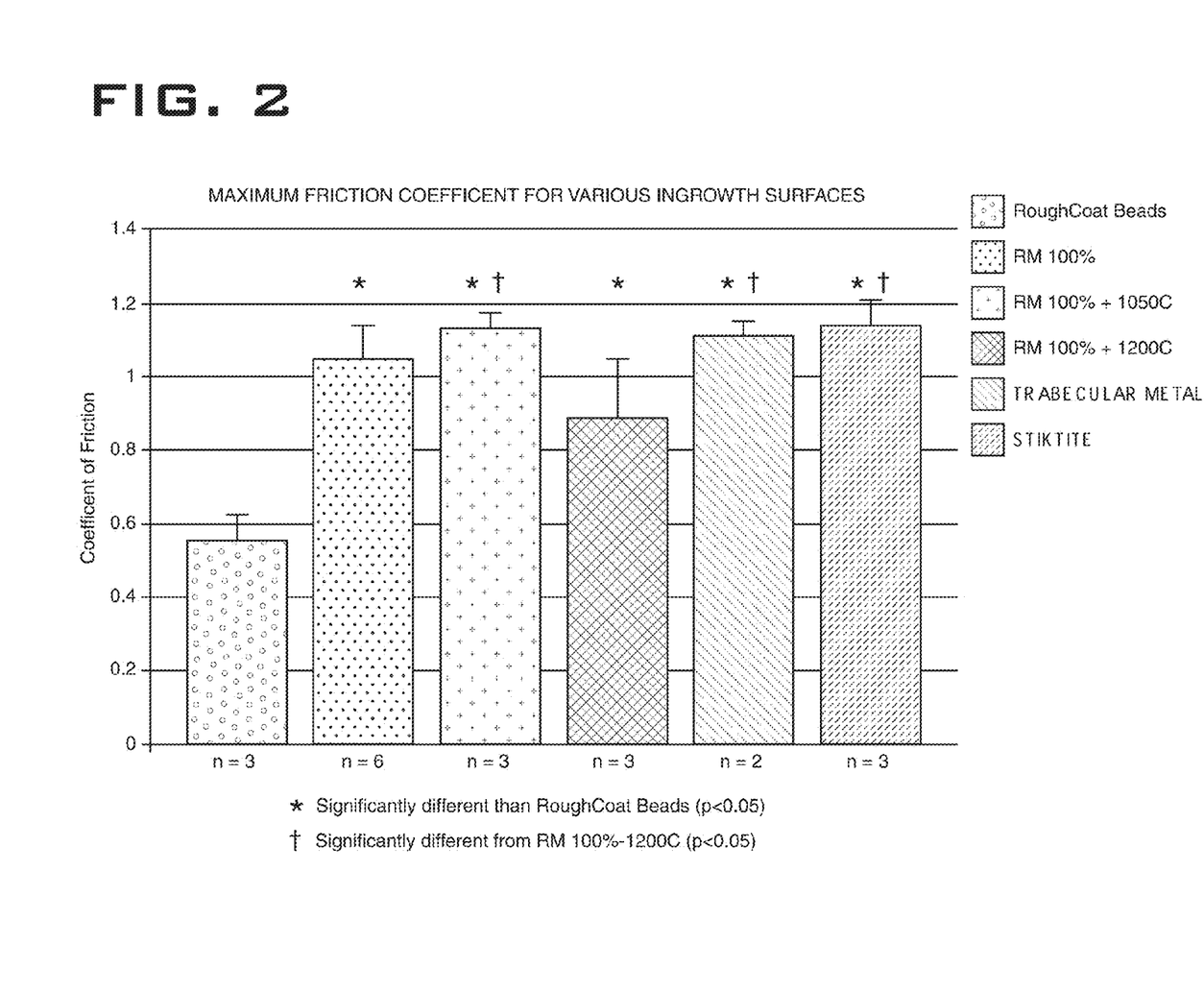
FIG. 2 is a graph comparing the coefficient of friction of various products, including exemplary porous structures treated according to the aspects of the present disclosure.

FIG. 2 is a chart of the average coefficient of friction of samples of six types of products. The first product was ROUGHCOAT beads, which is a commercially available porous in-growth surface. It consists of approximately 250-350 micron sized beads sintered on a solid substrate. The coefficient of friction of three samples of ROUGHCOAT beads were measured. Referring to FIG. 2, the average (±std. dev.) coefficient of the ROUGHCOAT beads samples was about 0.55±0.08.

The second product in the chart of FIG. 2 was a porous structure formed by RMT without any treatment, indicated as "RM 100%." The coefficient of friction of six different porous structures formed by RMT without any treatment were measured. The average (±std. dev.) coefficient for the RM 100% samples was about 1.04±0.08.

The third product was a porous structure formed by RMT that was treated according to the aspects of the present disclosure, specifically the samples were thermally treated at a temperature of 1050 C under vacuum ($<10^{-5}$ Torr) for a period of about 1 hour. These samples are indicated as "RM 100%+1050 C" on FIG. 2. The coefficient of friction of three different RM 100%+1050 C were measured. The average (±std. dev.) coefficient for the RM 100%+1050 C samples was about 1.13±0.04.

As reflected by FIG. 2, the heat treatment according to the aspects of the present disclosure increases the coefficient of friction of the porous structure as compared to the RM 100% samples, which are porous structures that have not been treated. The increase in friction indicates that this structure retained the desired asperities and thus, providing an increase in the benefits of a porous structure, e.g., improved cellular attachment due to higher stability as a result of higher friction, while the bonding strength between the micro-particles and the porous structure is improved.

The heat treatment, however, if not controlled can lead to detrimental effects, such as a decrease in the coefficient of friction of the porous structure. Referring to FIG. 2, the fourth product was a porous structure formed by RMT that was treated heat treated in the following conditions: 1200 degrees C. for 1 hour under vacuum ($<10^{-5}$ Torr). These samples are indicated as "RM 100%+1200 C" in FIG. 2. The coefficient of friction of three different RM 100%+1200 C were measured. The average (±std. dev.) coefficient for RM 100%+1200 C products was 0.88±0.16. The heat treatment at higher temperature actually decreases the coefficient of friction of the porous structure as compared to RM 100%, porous structures that have not been treated, and RM 100%+ 1050 C, porous structures that were treated at a lower temperature. The decrease in friction indicates that the surface area or the asperities of the porous structure has been reduced. While not intending to be bound by theory, it is believed the higher temperature melts a significant number of the micro-particles into the main body of the porous structure, thereby decreasing the asperities and surface area and thus, the coefficient of friction.

Figure 4A:
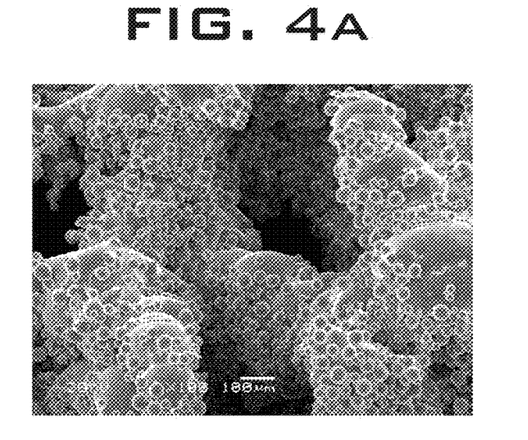
FIGS. 4A-4C illustrate various magnification images of loose particles attached to a strut and to each other.
Figure 4B:
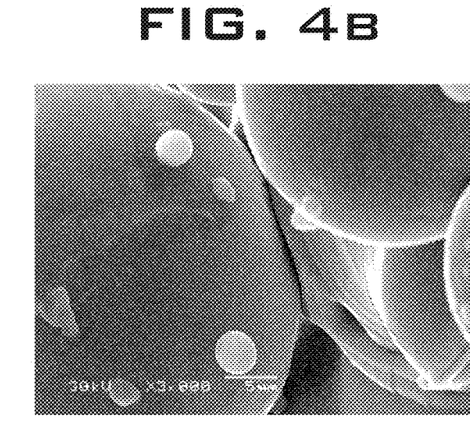
Figure 4C:
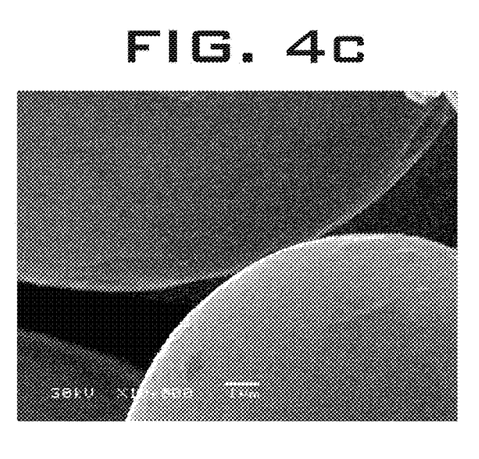
Figure 5:
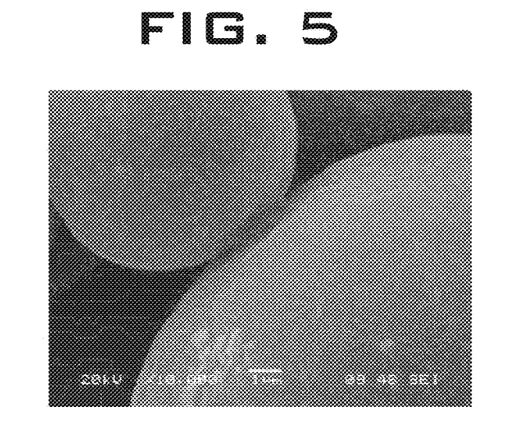
FIG. 5 illustrates effects of heat-treatment on loose particle specifically heat-treatment carried out at 800 C for 1 hour.
Figure 6:
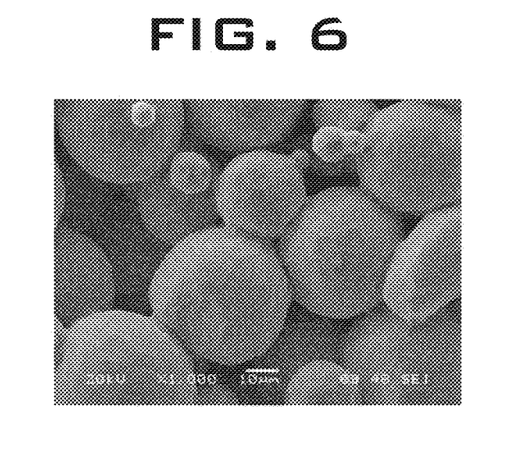
FIG. 6 illustrates effects of heat-treatment on loose particle specifically heat-treatment carried out at 1050 C for 2 hours.
Figure 7:
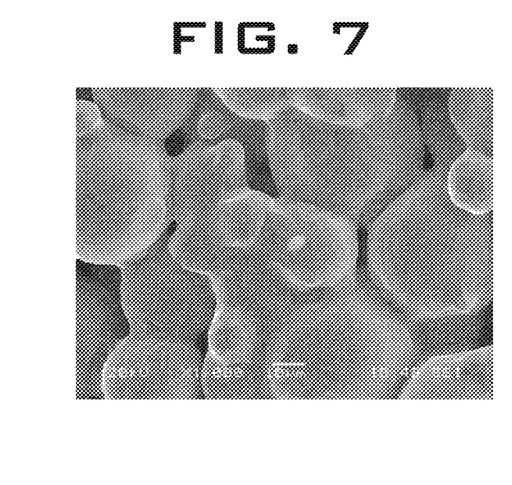
FIG. 7 illustrates effects of heat-treatment on loose particle specifically appearance of particles after sintering at 1200 C for 2 hours.

In order to explore this hypothesis, an experiment was conducted to evaluate the sintering of loose micro particles or beads to each other using Ti6Al4V powder that is used to build the porous RM structure. FIG. 4 shows low and high magnification images of loose particles attached to the strut and to each other. As can be seen some of the particles are barely attached to each other (FIG. 4C) and some have inadequately formed bonds (FIG. 4B). FIGS. 5 to 7 show how these loose particles will attach to each other when heat-treated at different temperatures. FIG. 5 shows heat-treatment carried out at 800 C for 1 hour. The particles still retain their spherical shape and some enhancement in the bonding of the particles has occurred. FIG. 6 shows heat treatment carried out at 1050 C for 2 hours. A significant bonding between the particles has now occurred without losing the spherical shape of the particles. Additionally, facets have formed on the surface of these micro particles which further enhance the surface area. FIG. 7 shows appearance of particles after sintering at 1200 C for 2 hours. A substantial melting of micro powder particles has not occurred and several micro particles have lost the spherical shape and thus substantially reducing the surface area. One way to evaluate the attachment of these particles to each other is to measure the ratio of the micro-particle diameter to the neck diameter (PD/ND). A higher ratio indicates inadequate bonding which may result in higher friction but also particle shedding. If the ratio BD/ND is close to 1, it indicates that the micro particles have almost melted into each other. The cross-sectional metallographic evaluation of samples shown in FIG. 6 showed an average PD/ND ratio of 2.1.

According to one aspect of this disclosure the heat treatment is carried out in such a way that the micro-particle diameter to neck diameter of the particulates attached to other particles or the strut is from 1.5 to 5.0. This ratio not only seems to keep the bonding of the particles well but also retains the surface area and thus the frictional characteristics of the structure. This ratio can be evaluated by standard cross-sectional metallographic techniques. The RM structure samples are sectioned, mounted, polished and measured using metallurgical microscope. At least five random fields of view are chosen to measure the micro particle diameter and neck diameter. A magnification of 25×, 50× or 100× is chosen for measurements. It is important to average the particle diameter if the particles are of significantly different in size and then divide by the neck diameter to get an accurate measure of the micro-particle diameter to neck diameter. If the multiple particles are attached to each other, an average of particle diameter and neck diameter is calculated for that group of particles or strut.

In some embodiments of the invention, the micro-particle diameter to neck diameter after the heat treatment can be from about 1.75 to about 4.00. In other embodiments, the micro-particle diameter to neck diameter after the heat treatment can be from about 1.8 to about 3.6.

Referring to FIG. 2, the fifth and sixth products are commercially available products that serve as standards to compare the coefficient of friction of the porous structures treated according to the aspects of the present disclosure.

The fifth product is TRABECULAR METAL currently manufactured by Zimmer, Inc. TRABECULAR METAL is a registered trademark of Zimmer, Inc. The coefficient of friction of two samples of TRABECULAR METAL were measured, and the average (±std. dev.) of the samples was 1.11±0.03.

The sixth product was STIKTITE which is manufactured by Smith and Nephew Inc. STIKTITE is a registered trademark of Smith & Nephew, Inc. This is generally produced by sintering asymmetrical titanium powder to create a porous surface. The coefficient of friction of three samples of STIKTITE were measured. The average (±std. dev.) friction coefficients of the STIKTITE samples was 1.14±0.07. As shown in FIG. 2, the friction coefficients of STIKTITE and TRABECULAR METAL are similar to the friction coefficients of the RM 100%+1050 C samples.

The porous structures of the present disclosure provide options that may not be available with the commercially available STIKTITE and TRABECULAR METAL products that have similar friction coefficients. For instance, STIKTITE is easy to produce and provides good frictional surface, but the finished product comprises a solid substrate on which asymmetrical Ti alloy powder is sintered, which may pose challenges in producing a fully porous structure of just STIKTITE.

While the TRABECULAR METAL can be produced as stand-alone porous structure, the production of this structure exclusively requires use of tantalum which is quite an expensive material. Additionally, the chemical vapor deposition process used to create this structure is not only lengthy but potentially hazardous in an environmental sense as chlorine gas is used to generate some of the reagents used for deposition.

According to one aspect of the present disclosure, thermal treatments that are less than about 800 degrees C. are insufficient to improve the attachment strength of the micro-particles, e.g., adequately bind the loose micro-particles. One exemplary way to determine whether the thermal treatment was sufficient to bind the loose micro-particles involves assessing the particle shedding of the RM structure by agitating the thermally treated samples in an ultrasonic bath containing deionized water. In one embodiment, samples to be tested are first weighed on a high-precision balance. The samples are then submerged in deionized water and subjected to ultrasonic vibration in an ultrasonic bath for an appropriate amount of time known to those skilled in the art, e.g., 4 minutes. The samples were removed after being subject to the ultrasonic vibration and rinsed with methanol, blown dry with compressed air, and preferably dried under vacuum for at least 2 hours. After drying, the samples were weighed again to determine the post-test weight. The differences in pre-test and post-test weight were used to determine the mass loss due to particle shedding.

In one specific example, the as-built samples (without the heat-treatment) lost about 6 mg. The samples that were heat-treated at about 800 degrees C. for about 1 hour in vacuum ($<10^{-4}$ Torr) lost about 0.3 mg while the samples that were heat-treated at about 1050 degree C. for about 1 hour and about 1200 degree C. for about 1 hour lost less than 0.02 mg. Accordingly, the heat treatment at about 800 degrees C. is insufficient to bind the loose micro-samples while heat treatments at higher temperatures improve the attachment strength of the micro-particles to the porous structure, retaining substantially all of the micro-particles on the porous structure. However, without performing the heat treatment according to the aspects of the present disclosure, the improved binding of the micro-particles can still result in undesirable effects for the treated porous structure as discussed herein.

In the preferred embodiment, the heat treatment can be optimized for the particular material of the porous structure. According to one aspect, the optimization is done by first determining a friction value, e.g., coefficient of friction, of the porous structure prior to any treatment. A temperature and time are selected for a first thermal treatment trial. The porous structure is then treated at this first round of thermal treatment with the selected conditions. The optimization continues with determining the friction value of the treated porous structure. If the friction value subsequent to treatment increases or remains substantially the same, the selected conditions are the desired conditions to increase bond strength of the micro-particles to the porous structure without substantially reducing the surface area of the porous structure. However, if the friction value subsequent to treatment decreases, then new temperature and time are selected for the next thermal treatment trial. The temperature should be decreased. If the temperature is insufficient to improve the bond strength of the micro-particles, the temperature should be increased. The optimization steps are repeated and the temperature and time are adjusted until the friction value subsequent to treatment is substantially the same as or higher than the friction value prior to treatment. In one embodiment, the selected time and temperature for said treatment results in the friction value prior to treatment being within about 0% to less than about 15% of the friction value subsequent to treatment. In another embodiment, the values are within about 5% to about 10% of the friction value subsequent to treatment. In another embodiment, the values are within about 10% to less than about 15% of the friction value subsequent to treatment. In another embodiment, the values are within about 8% to about 12% of the friction value subsequent to treatment.

The treated porous structure according to the aspects of the present disclosure can be used to form a medical implant. In one embodiment, the medical implant is selected from the group consisting an orthopedic implant, dental implant, and vascular implant. In one embodiment, the orthopedic implant is selected from a group consisting of hip, knee, shoulder, elbow, and spinal implants.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method comprising the steps of:
   forming a porous structure from a metallic material using a rapid manufacturing technique selected from the group consisting of direct metal fabrication and direct metal laser sintering; and
   treating the porous structure formed by the rapid manufacturing technique with a thermal treatment to increase the bond strength between a plurality of micro-particles partially fused to a surface of said porous structure and said porous structure without reducing the surface area of the porous structure and without reducing a coefficient of friction of the porous structure when the porous structure is articulated against an analogue component.

2. The method of claim 1, wherein the thermal treatment provides an average micro-particle diameter to neck diameter ratio greater than 1 and less than 5.

3. The method of claim 1, wherein the thermal treatment is selected from the group consisting of high vacuum furnace treatment, resistive heat treatment, radiative heat treatment, electron beam scanning, laser beam scanning, and a combination thereof.

4. The method of claim 1, further comprising the step of selecting the time and temperature for said thermal treatment, wherein said selection is configured to improve the bonding between said plurality of micro-particles and said porous structure while at least preserving a desired roughness and friction of said porous structure.

5. The method of claim 1, wherein the metallic material is selected from the group consisting of titanium, titanium alloy, zirconium, zirconium alloy, niobium, niobium alloy, tantalum, tantalum alloy, nickel-chromium, cobalt-chromium alloy and combinations thereof.

6. The method of claim 5, wherein the porous structure comprises titanium alloy, the temperature of the thermal treatment of the titanium alloy structure is between greater than 800 degrees C. and less than 1200 degrees C.

7. The method of claim 6, wherein the temperature of the thermal treatment of the titanium alloy structure is between 950 degrees C. and 1150 degrees C.

8. The method of claim 6, wherein the temperature of the thermal treatment of the titanium alloy structure is between 1000 degrees C. and 1100 degrees C.

9. The method of claim 6, wherein the temperature of the thermal treatment of the titanium alloy structure is between 1025 degrees C. and 1075 degrees C.

10. The method of claim 6, wherein the temperature of the thermal treatment of the titanium alloy structure is between 1040 degrees C. and 1060 degrees C.

11. The method of claim 1, wherein forming the porous structure comprises forming the porous structure from a Ti6A14V titanium alloy powder using the rapid manufacturing technique; and
    wherein treating the porous structure with the thermal treatment comprises treating the porous structured formed from the Ti6A14V titanium alloy with the thermal treatment to increase the bond strength between the plurality of micro-particles and said porous structure without reducing the surface area of the porous structure.

12. The method of claim 6, wherein the temperature of the thermal treatment of the titanium alloy structure is about 1050 degrees C.

13. The method of claim 6, further comprising selecting the temperature of the thermal treatment of the titanium alloy structure to be 1050 degrees C.

14. The method of claim 1, wherein the porous structure is thermally treated from about 30 minutes to 300 minutes.

15. The method of claim 14, wherein the porous structure is thermally treated from about 60 minutes to 180 minutes.

16. The method of claim 14, wherein the porous structure is thermally treated from about 90 minutes to 150 minutes.

17. The method of claim 14, wherein the porous structure is thermally treated for about 120 minutes.

18. The method of claim 1, wherein the thermal treatment is performed in a vacuum or inert gas furnace below atmospheric pressure.

19. The method of claim 18, wherein the thermal treatment is performed in a vacuum or inert gas furnace with oxygen partial pressure below about 10-4 torr.

20. The method of claim 18, wherein the thermal treatment is performed in a vacuum or inert gas furnace with oxygen partial pressure at or below about 10-5 torr.

21. The method of claim 1, wherein the thermal treatment is performed in a vacuum or inert gas furnace with oxygen partial pressure below about 0.02 torr.

22. The method of claim 1, wherein a time and temperature of the thermal treatment is determined based at least on the size of the plurality of micro-particles and the solid-state diffusion coefficient of the plurality of micro-particles.

23. The method of claim 1, wherein a time and temperature of the thermal treatment is determined based at least on the desired aspect ratio of the porous structure.

24. The method of claim 1, wherein the method further comprises the step of forming a medical implant with said treated porous structure.

25. The method of claim 24, wherein the medical implant is selected from the group consisting an orthopedic implant, a dental implant, and a vascular implant.

26. The method of claim 1, wherein rapid manufacturing technique is direct metal fabrication.

27. The method of claim 1, wherein rapid manufacturing technique is direct metal laser sintering.

28. The method of claim 1, wherein treating the porous structure with the thermal treatment comprises treating the porous structure with the thermal treatment to increase the bond strength between the plurality of micro-particles and the porous structure while increasing the surface area of the porous structure.

29. The method of claim 1, wherein treating the porous structure with the thermal treatment comprises treating the porous structure with the thermal treatment to increase the bond strength between the plurality of micro-particles and the porous structure while increasing a coefficient of friction of the porous structure.

30. The method of claim 1, wherein the thermal treatment is a high vacuum furnace treatment.

31. The method of claim 1, wherein treating the porous structure with the thermal treatment comprises treating the porous structure with the thermal treatment to increase the bond strength between the plurality of micro-particles and the porous structure without completely melting the micro-particles into a main body of the porous structure.

32. The method of claim 1, wherein treating the porous structure with the thermal treatment comprises treating the porous structure with the thermal treatment to increase the bond strength between the plurality of micro-particles and the porous structure without reducing the surface area of the porous structure such that the surface area of the thermal treated porous structure is at least equal to a surface area of the porous structure prior to the thermal treatment.

33. The method of claim 1, wherein the metallic material is selected from the group consisting of titanium, titanium alloy, and stainless steel.

34. The method of claim 1, wherein the metallic material comprises titanium alloy.

35. A method, comprising:
forming a porous structure from a metallic material using a rapid manufacturing technique selected from the group consisting of direct metal fabrication and direct metal laser sintering; and
treating the porous structure formed by rapid manufacturing technique with a thermal treatment to increase the bond strength between a plurality of micro-particles partially fused to a surface of said porous structure and said porous structure without reducing the surface area of the porous structure and without reducing a coefficient of friction of the porous structure when the porous structure is articulated against an analogue component, wherein the rapid manufacturing technique is selected from group consisting of direct metal fabrication, direct metal laser sintering, and solid free-form fabrication; and
further comprising the step of selecting the time and temperature for said thermal treatment, wherein said selection is configured to improve the bonding between said plurality of micro-particles and said porous structure while increasing the roughness of said porous structure.

36. A method comprising the steps of:
treating a porous structure formed from a metallic material using a rapid manufacturing technique with a thermal treatment to increase the bond strength between a plurality of micro-particles attached to said porous structure and said porous structure, wherein the rapid manufacturing technique is selected from group consisting of direct metal fabrication, direct metal laser sintering, and solid free-form fabrication; and
selecting a time and temperature for said thermal treatment, wherein the time and temperature of the thermal treatment is determined based at least on the desired friction of a surface of the porous structure;
wherein the selecting step comprises determining a friction value of said porous structure prior to treatment, determining a friction value of said porous structure subsequent to treatment, adjusting the time and temperature of said treatment until the friction value subsequent to treatment is greater than or equal to the friction value prior to treatment; and
wherein the friction value comprises a coefficient of friction when said porous structure is articulated against an analogue component.

37. The method of claim 36, wherein the selecting step comprises determining a friction value of said porous structure prior to treatment, determining a friction value of said porous structure subsequent to treatment, adjusting the time and temperature of said treatment until the friction value subsequent to treatment is higher than said friction value prior to treatment.

38. The method of claim 36, wherein the selected time and temperature for said treatment results in the friction value prior to treatment being within about 0% to less than about 15% of the friction value subsequent to treatment.

39. The method of claim 38, wherein the selected time and temperature for said treatment results in the friction value prior to treatment being within 5% to 10% of the friction value subsequent to treatment.

40. The method of claim 38, wherein the selected time and temperature for said treatment results in the friction value prior to treatment being within 10% to less than 15% of the friction value subsequent to treatment.

41. The method of claim 38, wherein the selected time and temperature for said treatment results in the friction value prior to treatment being within 8% to 12% of the friction value subsequent to treatment.

42. The method of claim 36, wherein the friction and or roughness of said porous structure is measured using an inclined plane method or using a pin-on-disk testing apparatus.

43. The method of claim 42, wherein the pin-on-disk method provides the friction value at the beginning of the motion and also during the motion.

44. The method of claim 36, further comprising:
selecting a metallic material from the group consisting of zirconium, zirconium alloy, niobium, niobium alloy, tantalum, tantalum alloy, nickel-chromium, cobalt-chromium alloy and combinations thereof; and
forming the porous structure from the selected metallic material using the rapid manufacturing technique; and
wherein treating the porous structure with the thermal treatment comprises treating the porous structured formed from the selected metallic material with the thermal treatment to increase the bond strength between the plurality of micro-particles and said porous structure without reducing the surface area of the porous structure.

* * * * *